US00RE40022E

(19) United States
(12) Reissued Patent
Fencl et al.

(10) Patent Number: US RE40,022 E
(45) Date of Reissued Patent: Jan. 22, 2008

(54) GERMICIDAL LAMP FOR HARSH ENVIRONMENTS

(75) Inventors: Forrest B. Fencl, Huntington Beach, CA (US); Robert M. Culbert, Cerritos, CA (US)

(73) Assignee: Steril-Aire, Inc., Burbank, CA (US)

(21) Appl. No.: 10/706,483

(22) Filed: Nov. 12, 2003

(Under 37 CFR 1.47)

Related U.S. Patent Documents

Reissue of:
(64) Patent No.: 6,372,186
Issued: Apr. 16, 2002
Appl. No.: 09/241,948
Filed: Feb. 2, 1999

U.S. Applications:
(63) Continuation-in-part of application No. 08/773,643, filed on Dec. 24, 1996, now Pat. No. 5,866,076.

(51) Int. Cl.
*A61L 9/20* (2006.01)

(52) U.S. Cl. ..... 422/121; 250/453; 250/436; 96/224; 362/645

(58) Field of Classification Search ..... 422/121; 250/435, 436; 362/226, 645, 652; 96/224
See application file for complete search history.

(56) References Cited

U.S. PATENT DOCUMENTS 2,365,342 A * 12/1944 Hilliard et al. ..... 315/48
2,586,940 A * 2/1952 Graham et al. ..... 604/179
2,778,588 A * 1/1957 Capocci ..... 248/112
3,576,593 A * 4/1971 Cicirello ..... 422/4
4,179,616 A * 12/1979 Coviello et al. ..... 422/186.3
4,390,432 A * 6/1983 Takeguchi et al. ..... 210/748
4,971,687 A * 11/1990 Anderson ..... 210/85
4,990,313 A * 2/1991 Pacosz ..... 96/224
5,151,174 A * 9/1992 Wiesmann ..... 210/97
5,266,215 A * 11/1993 Engelhard ..... 210/748
5,334,347 A * 8/1994 Hollander ..... 422/24
5,334,905 A * 8/1994 Ullrich ..... 313/22
5,505,904 A * 4/1996 Haidinger et al. ..... 422/24
5,660,719 A * 8/1997 Kurtz et al. ..... 210/85
5,701,050 A 12/1997 Wolf
5,742,063 A 4/1998 Scroggins
5,853,299 A 12/1998 Wu
5,866,076 A * 2/1999 Fencl et al. ..... 422/121
5,894,130 A 4/1999 Bach
5,902,552 A 5/1999 Brickley
6,221,314 B1 4/2001 Bigelow
6,248,235 B1 6/2001 Scott
6,261,449 B1 7/2001 Scott
6,274,049 B1 8/2001 Scott
6,330,947 B1 12/2001 Scott
6,508,367 B2 1/2003 Scott
6,524,457 B1 2/2003 Scott

FOREIGN PATENT DOCUMENTS

WO WO 95/17634 * 6/1995

OTHER PUBLICATIONS

Light Sources, Inc.; Germipak UV Cells Spec Sheet.*
Light Sources, Inc., Your Own Style Lamp Base brochure.*
Modern Medical Systems, Products and Systems for Protection for Airborne Tuberculosis Bacillus brochure.*
Block, Seymour S., ed. Disinfection, Sterilization, and Preservation, 4th ed. 1991. p. 555.*

* cited by examiner

*Primary Examiner*—E. Leigh McKane
(74) *Attorney, Agent, or Firm*—SoCal IP Law Group LLP; Steven C. Sereboff; John E. Gunther

(57) ABSTRACT

A germicidal lamp for harsh environments is disclosed. The germicidal lamp is suited for outdoor installation on an HVAC system or related components. The germicidal lamp is made from materials resistant to splashing water, etc., and includes plural seals to protect the interior of the fixture and prevent leakage or contamination into or out of the HVAC system.

35 Claims, 6 Drawing Sheets

GERMICIDAL LAMP FOR HARSH ENVIRONMENTS

Matter enclosed in heavy brackets [ ] appears in the original patent but forms no part of this reissue specification; matter printed in italics indicates the additions made by reissue.

RELATED APPLICATION INFORMATION

This application is a continuation-in-part of application Ser. No. 08/773,643, filed Dec. 24, 1996 entitled "Single-Ended Germicidal Lamp for HVAC Systems," issued Feb. 2, 1999 as U.S. Pat. No. 5,866,076, which is incorporated herein by reference.

This application is related to application Ser. No. 08/803,350 filed Feb. 20, 1997 entitled "Method of UV Distribution in an Air Handling System," issued Oct. 6, 1998 as U.S. Pat. No. 5,817,276, which is incorporated herein by reference.

This application is related to application Ser. No. 09/167,376 filed Oct. 6, 1998 entitled "Reduction of Energy Consumption in a Cooling or Heating System Through UVC Irradiation," which is incorporated herein by reference.

This application is related to application Ser. No. 09/170,361 filed Oct. 13, 1998 entitled "Returning a Heat Exchanger's Efficiency to "As New," which is incorporated herein by reference.

This application is related to application Ser. No. 09/173,081 filed Oct. 14, 1998 entitled "Reduction of Pressure Drop of a Cooling or Heating System."

This application is related to application Ser. No. 09/172,638 filed Oct. 14, 1998 entitled "Control of Health Hazards in an Air Handler."

This application is related to application Ser. No. 09/172,637 filed Oct. 14, 1998 entitled "Cleaning and Maintaining a Drain Pan in an Air Handling System."

NOTICE OF COPYRIGHTS AND TRADE DRESS

A portion of the disclosure of this patent document contains material, which is subject to copyright protection. This patent document may show and/or describe matter, which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

BACKGROUND OF THE INVENTION

1. Field of the Invention

The present invention relates generally to germicidal lamps, and more particularly the invention relates to such devices used in air and surface sterilization.

2. Description of Related Art

One industry that is mature and economically sensitive to costs is the heating, ventilation and air conditioning (HVAC) industry. Because of the competitive nature of both the construction and HVAC industries, HVAC systems must be inexpensive to purchase and install. Of a more global interest though, is the cost to operate and maintain HVAC systems. Often, a building owner will replace an aging HVAC system as the reduction in operating and maintenance costs can offset the retrofit cost, sometimes in a matter of months.

Broad social and energy policies also favor efficient HVAC systems. In these days of electricity conservation and deregulation, it has become even more important to conserve energy consumption. Recently, entire electrical grids have shut down on very hot days in part because of the huge electrical demand from inefficient HVAC systems running at extreme capacity. Furthermore, energy conservation translates directly into improved environmental conditions and decreased reliance upon foreign petroleum.

HVAC systems are typically comprised of a cooling and heating section for, respectively, cooling and heating the air. An HVAC system will also include fans and ductwork for moving this conditioned air where it is needed. In most HVAC systems, air is drawn in, filtered, cooled and dehumidified or heated and humidified, and then delivered to a space. The greatest portion of this air is drawn from the space for recirculation through the HVAC system.

One factor impacting design and operation of HVAC systems is indoor air quality (IAQ). A major consideration in IAQ today is the amount of outdoor air introduced by an HVAC system into an otherwise sealed space. The HVAC industry and others have adopted standards for the introduction of outdoor air into spaces serviced by an otherwise closed HVAC system. These include offices, residential, commercial, industrial and institutional spaces, and modes of transportation such as cars, buses, planes and ships. In addition to controlling indoor air for occupant comfort, the goal of most HVAC systems is to provide air with reduced levels of particulate, gases and bioaerosols, be it for semiconductor, pharmaceutical or food processing facilities, hospitals, schools or offices and now the home.

Various reasons have contributed to the lack of success in utilizing germicidal lamps for bioaerosol control (IAQ), except for limited and specialized purposes. The functional implementation of such devices in air moving systems has been limited generally to expensive portable units with questionable efficacy. However, non-moving air devices can be found as wall or ceiling mount systems where the germicidal lamp is situated in a minimum air movement, and proper ambient air temperature area. A typical germicidal tube is designed to operate in still air at 80–90° F. Germicidal lamps have sensitive physical characteristics, including their plasma gases, mercury and the partial pressures thereof.

When a conventional germicidal lamp is used to irradiate moving airstreams, the air moving across the tube removes heat and lowers the tube's temperature. The tube's mercury then condenses such that the emission of the germicidal wavelength of 253.7 mm decreases. This decrease can be up to 75% when the tube wall temperature reaches 58° F. Also, at lower internal temperatures, tube components degrade quicker, shortening tube life. This phenomenon, known as skin effect cooling, requires a notable increase in the number of conventional tubes required for a given level of performance. Increasing the number of tubes reduces the available square or open area for airflow. This in turn requires the airs' velocity to increase, which decreases the dose (time times intensity) and air volume. If such a system could be made to work, it would require an increase in fan horsepower, light energy and in the number of expensive tube replacements.

Conventional germicidal lamps emit ultraviolet light at both the primary and secondary emission lines of mercury (254 nm and 187 nm). At mercury's 187-nm line, ozone is created and in many applications of germicidal lamps, such as in water, ozone is desirable. However, ozone has strict threshold limit values in air due to its strong oxidative properties and potential harm to humans. Although numerous companies have attempted to apply germicidal lamps to HVAC systems, standard germicidal lamps have proved unsatisfactory. Typically, a conventional germicidal lamp performs best when installed in a system or room where the air is still and/or warm. Despite the clear benefits of germicidal lamps, problems such as decreased output in moving and/or low temperature air, reduced air changes and ozone production have prevented their use in all but specialized environments.

Germicidal fixtures continue to enter the HVAC market. Recent entries have been sold under the Germ-O-Ray and Germitroll trademarks. The particular capabilities and design of these devices is not known to the inventors, though it is believed both devices use conventional tubes that will suffer from the criteria outlined above when installed in air ducts.

For further information concerning improvements in electric discharge devices, which are directed to overcoming such problems, reference is made to the above-identified patent applications. These other patent applications describe excellent devices and methods for using germicidal lamps to make HVAC systems more efficient, less costly to operate and maintain, and to provide better IAQ for a healthier environment.

Germicidal tubes differ significantly from electric discharge devices used in ultraviolet gas spectroscopy (VUV tubes). Germicidal tubes are low-pressure types that emit UV light at the primary and secondary emission lines of mercury—254 nm and 187 nm. In contrast, VUV tubes are high-pressure types that operate at high temperatures and as a consequence, emit different spectral lines and intensities.

Besides IAQ standards that include HVAC systems, there are numerous other standards that apply to HVAC systems, their design, construction and components. One set of standards that applies to HVAC (and other) electrical equipment has been promulgated by the National Electrical Manufacturers Association (NEMA). NEMA has published standards regarding enclosures for electrical equipment including HVAC equipment installed outdoors. A NEMA Type 4 enclosure is constructed for outdoor use and provides a degree of protection against rain, sleet, snow and the formation of ice. A NEMA Type 4 enclosure also provides a degree of protection against windblown dust, dirt, splashing water, hose-directed water and corrosion. A NEMA Type 4 enclosure should protect personnel against incidental contact with the enclosed equipment. Additional information is available from the NEMA Web site at www.nema.org.

One common use of germicidal lamps is in water treatment where ozone is generally considered desirable. However, the ozone in these water treatment systems is controlled and not released to the atmosphere. Furthermore, their ultraviolet tubes are enclosed in a quartz sleeve to create an insulating, dead air space, thereby elevating the tubes' ambient operating temperature. This is necessary because the water would otherwise draw heat away from the tube in the same manner as air or as in skin effect cooling.

Germicidal lamps for water treatment must have some amount of protection from the water itself. In particular, these lamps are sleeved and further isolated in some manner to be water tight against and compared to the water vessel in which the tube is installed. However, water application fixtures have not been considered or used in air treatment systems. Also, water application fixtures have not been produced for HVAC use or for air treatment use in outdoor applications.

SUMMARY OF THE INVENTION

The invention includes a germicidal lamp adapted for mounting on a duct wall or other surface of an HVAC system, wherein the germicidal lamp's fixture and its interface with the duct wall or other surface are ruggedized to withstand outdoor elements. The germicidal lamp's interface with its power supply has been ruggedized to withstand outdoor elements.

The invention also includes methods of providing UVC irradiation from outside to within components of HVAC systems which are exposed to the elements.

The invention includes the germicidal lamps described herein, as well as an air conveyance system comprising such a germicidal lamp, and an HVAC system comprising such a germicidal lamp. The invention further includes methods of installing and using a germicidal lamp in an air conveyance system and an HVAC system.

Still further objects and advantages attaching to the device and to its use and operation will be apparent to those skilled in the art from the following particular description.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

These and additional embodiments of the invention may now be better understood by turning to the following detailed description wherein an illustrated embodiment is described.

DETAILED DESCRIPTION OF THE INVENTION

Throughout this description, the preferred embodiment and examples shown should be considered as exemplars, rather than limitations on the apparatus and methods of the present invention.

Figure 1:
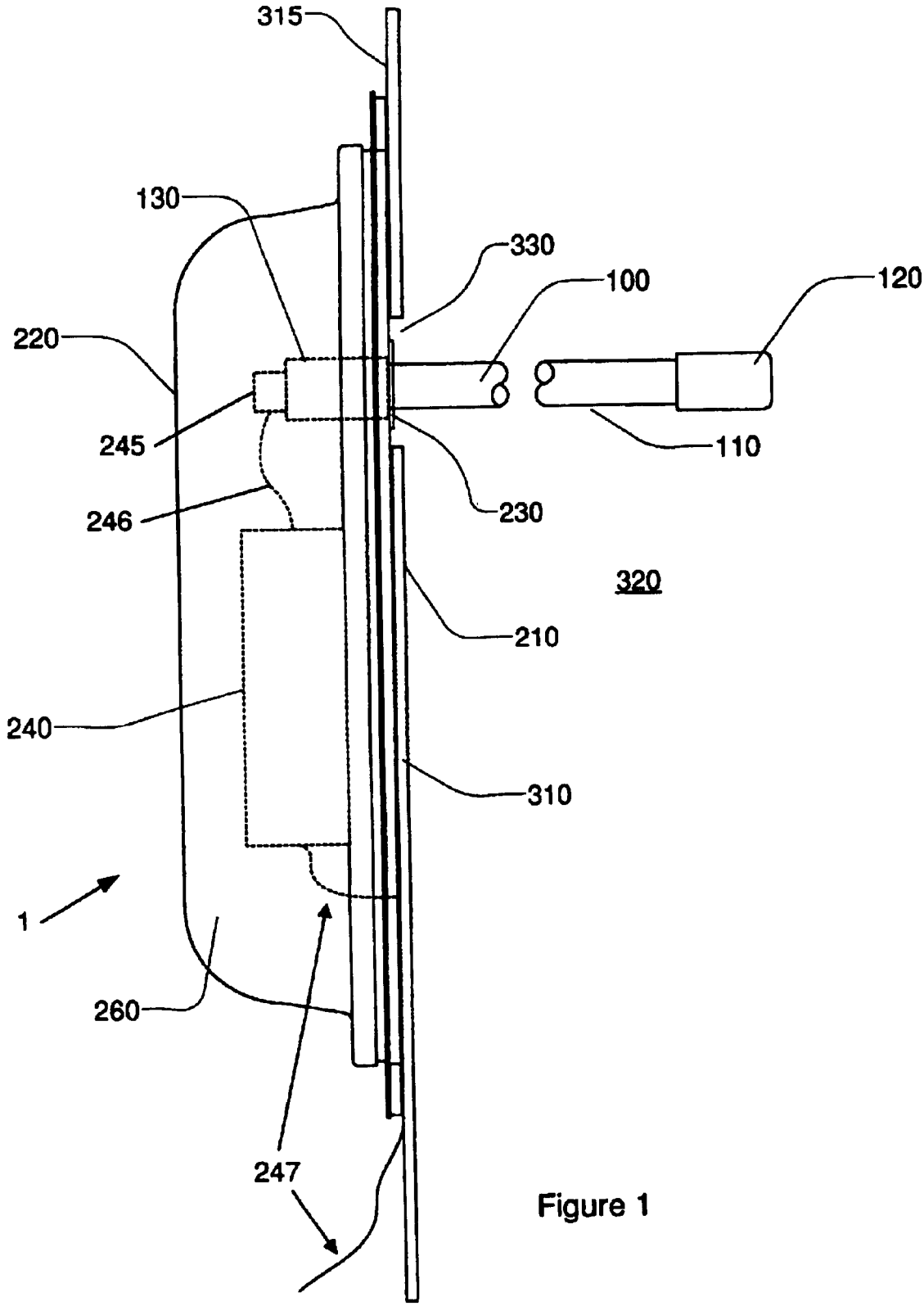
FIG. 1 is a side view of a germicidal lamp for external mounting.

Referring now to FIG. 1, there is shown a mounted germicidal lamp 1. The germicidal lamp 1 comprises a tube 100 and a fixture 200. FIG. 1 shows the germicidal lamp 1 mounted horizontally. The germicidal lamp 1 may also be mounted vertically or in other positions, so long as the fixture 200 includes sufficient support, as discussed below.

For exemplary purposes, the germicidal lamp 1 is shown installed on a wall 310 with an outer surface 315. The wall 310 defines an air passage 320 within the HVAC or air conveyance system, and may be the wall of an air duct, and air handler, or other portion of an HVAC system which defines a space through which air passes. The air passage 320 preferably has a volume which is from four to over fifty times greater than the volume of the tube 100 depending on the application.

The fixture 200 is attached to the outer surface 315 of the wall 310. The tube 100 extends from within the fixture 200 through an insertion hole 330 in the wall 310 and into the air passage 320. In general, HVAC systems do not have openings suitable for use as described and the insertion hole 330 must be created during installation of the germicidal lamp 1.

The insertion hole 330 should be small enough that the fixture 200 will entirely cover the insertion hole 330, thereby closing air leaks. Preferably, the insertion hole 330 is made slightly larger than the tube 100 so that the envelope 110 of the tube 100 may pass there through.

The germicidal lamp 1 preferably is light enough that the wall 310 can support the full weight of the germicidal lamp 1. The walls of typical HVAC systems are designed to hold their own weight and the weight of environmental elements. However, the weight-bearing capabilities of a target wall will not be unlimited. Therefore, the germicidal lamp 1 preferably has an installed weight below five pounds, and more preferably an installed weight of less than three pounds. In contrast, since weight is not usually an important factor for germicidal lamps, typical germicidal lamps are believed to weigh in excess of 5 pounds. Typical high output UVC lamps, such as those used for water purification, weigh considerably more than 5 pounds.

The tube 100 comprises a low-pressure germicidal tube. The tube 100 is preferably provided with power of a quality and quantity designed for the tube 100. The tube should be of the type which, when energized, emits UVC, primarily 254 nm, without substantial ozone and can withstand skin effect cooling. Preferably, the tube 100 is a UVC Emitter™, sold by Steril-Aire U.S.A., Inc. (Cerritos, Calif.), the assignee hereof. The tube 100 includes an envelope 110 and a stem 130. The tube 100, and particularly the envelope 110, preferably comprises an elongated hollow cylinder. The preferred tube 100 includes a first filament seated in the stem 130 and a second filament seated at the opposite end 120 of the envelope 110. Preferably wires (not shown) extend from the stem 130 to the filament in the opposite end 120.

The tube 100 preferably has UVC output characteristics which render it compatible with an HVAC system. Many of the air passages within an HVAC system are below room temperature and cold. Furthermore, HVAC systems are designed to move large amounts of air. Thus, the UVC output of the tube 100 preferably peaks when an air velocity of between 200 fpm and 600 fpm at between 30° F. and 65° F. is passed across the tube 100. More preferably, the UVC output from the tube 100 peaks when an air velocity of 400 fpm at 55° F. is passed across the tube 100. The tube 100 preferably can emit UVC of at least 10 $\mu W/cm^2$ per inch arc length, at one meter, when an air velocity of between 100 and 800 fpm is passed across the tube. Furthermore, the tube 100 preferably can emit UVC of at least 10 $\mu W/cm^2$ per inch arc length, at one meter, in an environment having a temperature between 35° F. and 170° F. and a relative humidity of up to 100%.

The fixture 200 comprises a cover 220, a base 210 and a tube-holder (not shown, discussed below). The cover 220 and the base 210 include exterior surfaces which are resistant to splashing water, hose-directed water, ice formations, wind, dirt, rain, and environmental corrosion. Preferably, the cover 220 and base 210 are made of 0.030 stainless steel or other materials which are strong, smooth and resistant to corrosion. The cover 220 and base 210 are preferably thick enough to be rigid and withstand external impacts from debris and maintenance tools. Furthermore, the fixture 200 and other parts described herein as appropriate preferably are constructed of materials, which will not break down from UV exposure, environmental exposure, or exposure to changes in heat and humidity as found in HVAC systems.

Figure 2:
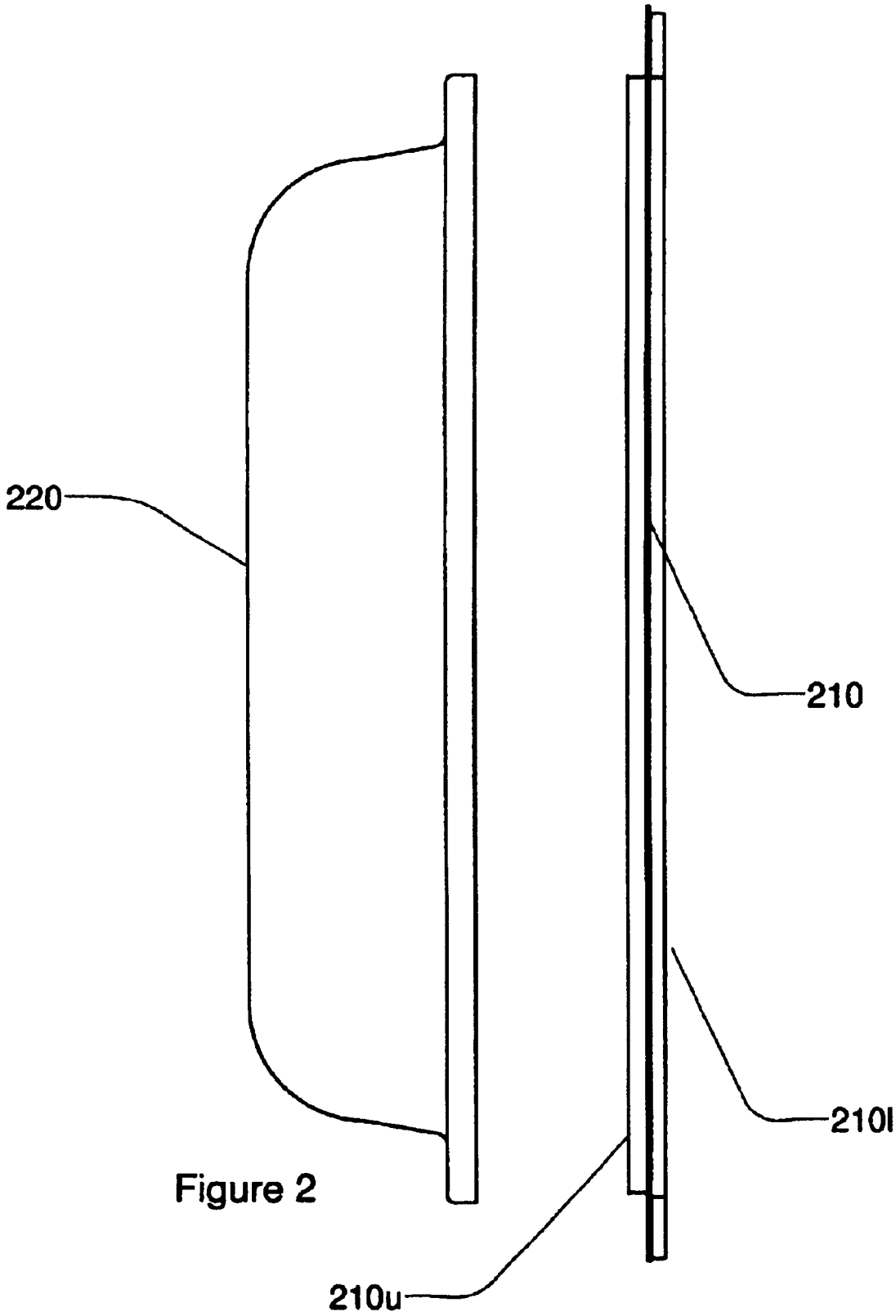
FIG. 2 is a side view of the germicidal lamp of FIG. 1 with the cover and base separated.

As shown in FIG. 2, the base 210 has an upper surface 210u and a lower surface 210l. The lower surface 210l of the base 210 seals against the wall 310 to thereby prevent splashing water, hose-directed water, ice formations, wind, dirt, rain and environmental corrosion to pass there through. The cover 220 and the upper surface 210u of the base 210 define an interior space 260 within the fixture (FIG. 1). The cover 220 seals tightly to the base 210 to thereby prevent splashing water, hose-directed water, ice formations, wind, dirt, rain and environmental corrosion from entering the interior space 260 of the fixture 200.

Figure 3:
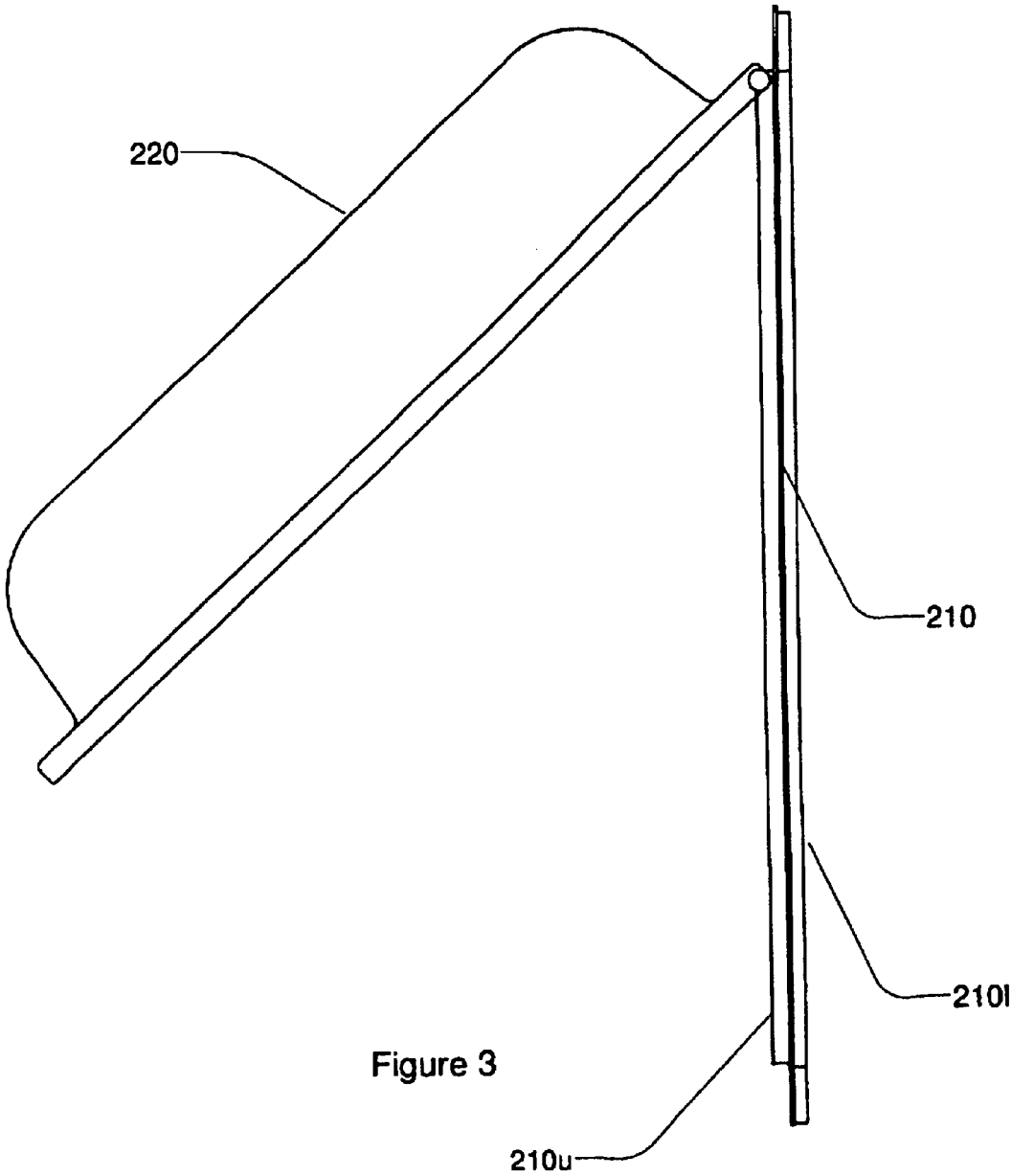
FIG. 3 is a side view of an alternative to the germicidal lamp of FIG. 1 with the cover and base separated.

The cover 220 is at least partially detachable from the base 210. The cover 220 can be, as desired, opened to allow access to the interior space 260 and closed to seal the interior space 260. The cover 220 preferably can either be completely separated from the base 210 (FIG. 2), or the cover 220 and the base 210 of the fixture 200 have a clamshell design (FIG. 3). It should be appreciated that FIGS. 2 and 3 show only the cover 220 and the base 210; the other components are not shown for clarity.

Referring again to FIG. 1, the base 210 includes an opening 230 through which the envelope 110 of the tube 100 is passed for installation of the tube 100 in the fixture 200 and removal of the tube 100 from the fixture 200. Installation and clamping the tube 100 preferably seals the opening 230 in the base 210 of the fixture 200 from air flow from the air passage 320 to the interior space 260. Installation and clamping the tube 100 preferably seals the opening 230 in the base 210 of the fixture 200 from air flow from the air passage 320 to outside the germicidal lamp 1.

The fixture 200 preferably includes a power supply 240. The power supply 240 may be of the type known in the art as a ballast and is provided for converting any available electrical power into a form appropriate and ideal for driving the tube 100 as described above. Preferably, the power supply 240 is electronic (i.e., not magnetic) and outputs 450 V to start the tube and 40–55 V at from 28 to 65 kHz during normal operation. This is the preferred power supply 240 for the UVC Emitters described above. Preferably, the power supply 240 is attached to the upper surface 210u of the base 210. However, the power supply 240 may alternatively be located outside of the fixture 200, separate from the germicidal lamp 1. For example, the power supply 240 may be positioned within an HVAC units' electrical components housing (not shown).

There is preferably also provided an electrical connector 245 disposed within the fixture adapted to electrically engage the stem 130 of the tube 100 to the power supply 240 via plural wires 246.

Plural electrical leads 247 are provided to connect the power supply 240 to an outside source of power. Preferably, the electrical leads 247 include piggyback connectors adapted to be connected to an air conditioner's fan power controller. In this way, other connectors on the fan power controller can be removed from the fan power controller and attached to the electrical leads 247 of the piggyback connector, and the piggyback connector can then be attached to the fan power controller in place of the original connector.

Plural-tube embodiments are also within the scope of the invention. Plural tube germicidal lamps provide the advantage of additional UV energy disbursement inside the duct while reducing the time needed to install the lamp. These embodiments also result in reduced cost of the fixture, since the plural tubes share a single housing and power supply and shipping and storage is simplified.

The Preferred Sealing Means

As set forth above, the germicidal lamp of the invention has a number of features which render it impervious to splashing water, hose-directed water, ice formations, dirt, wind, rain and environmental corrosion. This aspect of the germicidal lamp of the invention is believed to be one patentable distinction from the prior art. Although UV lamps have been used for water treatment, no germicidal lamp suitable for use in moving and/or cold air conditions has been known which also is suitable for use in harsh environmental conditions. It is believed that such a germicidal lamp has not been considered in the past because germicidal lamps have generally been considered unsuitable for most moving and/or cold air applications, especially HVAC systems.

In addition to the materials of the fixture 200, there are a number of interfaces,. which preferably are sealed. These interfaces include the cover 220 to base 210, base 210 to wall 310, and tube stem 130 to base 210. Preferably, each of these interfaces is sealed with an appropriate seal.

The various sealing means are preferably of closed cellular foam to solid rubber, so as to be pliable sufficient enough to provide a minimum 50% to 10% compression across the surface area put to use and from the intended force exerted, and to be impervious to the environmental elements of the intended application as well as ozone, ultraviolet light, solvents, cleaners, petrochemicals and abrasion.

Figure 4A:
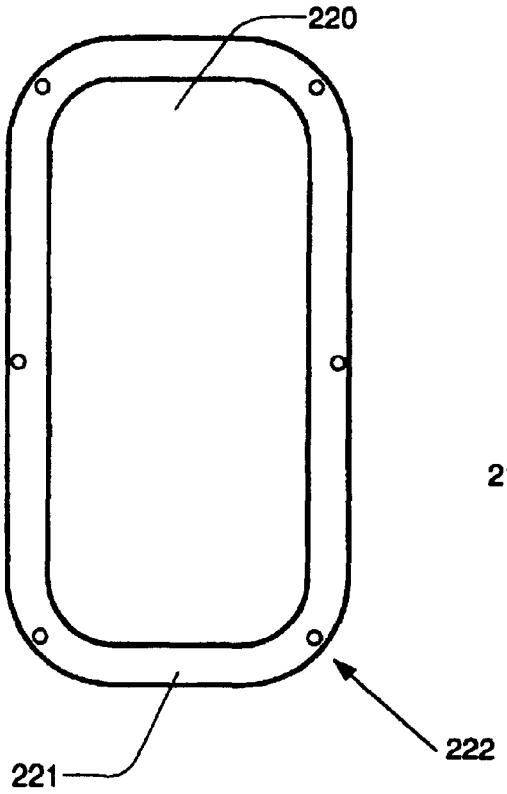
FIG. 4A is a base view of the cover of the germicidal lamp of FIG. 1.

As shown in FIG. 4A, the cover 220 preferably includes a cover gasket 221. The cover gasket 221 is preferably a single smooth piece of silicon rubber having a constant thickness, which runs around the perimeter of the cover 220. Preferably, the cover 220 and/or the upper surface 210u of the base 210 include a groove or depression into which the cover gasket 221 aligns and partially rests. This allows easier installation of the cover gasket 221 and also decreases gasket run-out, which increases the likelihood of a proper seal. The cover 220 and the base 210 also preferably include a number of screw holes 222, 212 through which screws may be fitted to hold the cover 220 to the base 210, and therefore the cover gasket 221 in place. The cover gasket 221 preferably also includes complementary holes, although the cover gasket 221 could be made to sit just inside or just outside of the screw holes 222, 212. The cover 220 and the base 210 preferably seal to air pressure of at least 20 inches of water gage.

Figure 4B:
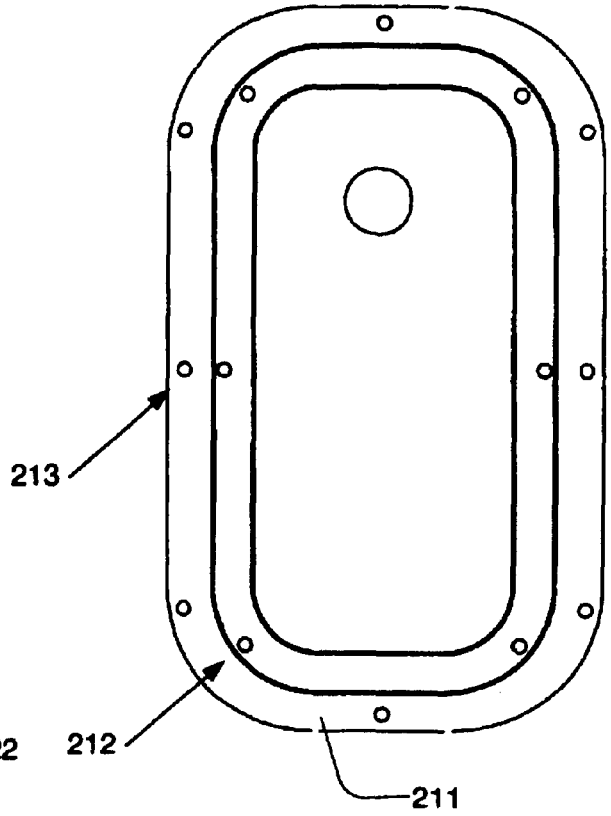
FIG. 4B is a base view of the base of the germicidal lamp of FIG. 1.

As shown in FIG. 4B, the base 210 preferably includes a base gasket 211. The base gasket 211 is preferably a single smooth piece of silicon rubber having constant thickness, which runs around the perimeter of the lower surface 2101 of the base 210. Preferably, the lower surface 210l of the base 210 includes a groove or depression into which the base gasket 211 aligns and partially rests. This allows easier installation of the base gasket 221 and also increases the likelihood of a proper seal to irregular surfaces. The base 210 also preferably includes a number of screw holes 213 through which screws may be fitted to hold the base 210 to the wall 310, and therefore the base gasket 211 in place. The base gasket 211 preferably also includes complementary holes, although the base gasket 211 could be made to sit just inside or just outside of the screw holes 213. The base 210 and the wall 310 preferably seal to air pressure of at least 15 inches of water gage.

Figure 5:
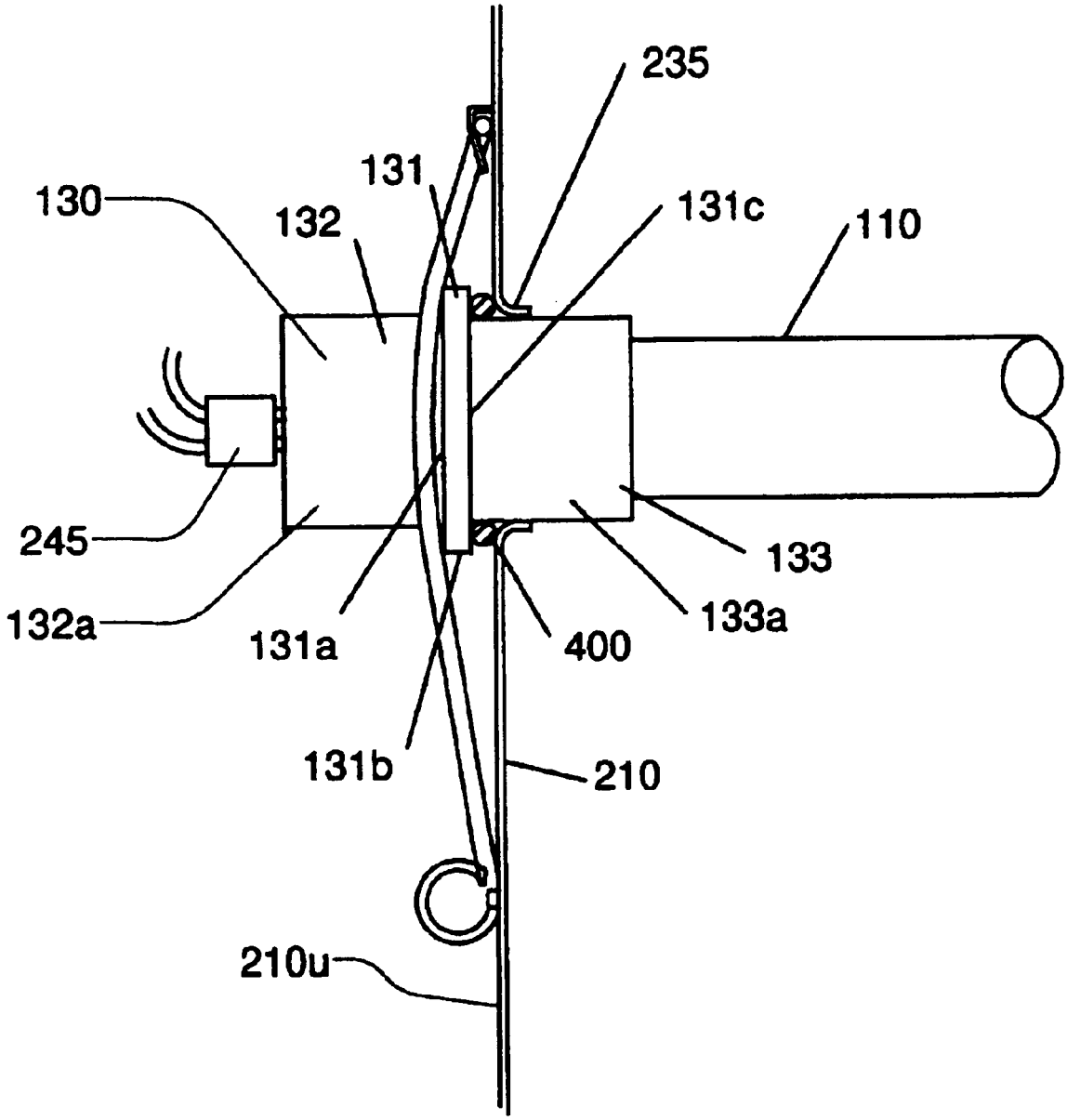
FIG. 5 is a side view of a tube holder in accordance with the invention.

As shown in FIG. 5, a tube gasket 400 is preferably disposed between the stem 130 of the tube 100 and the upper surface 210u of the base 210. The tube gasket 400 is preferably a single smooth piece of silicon rubber having constant thickness which runs around the opening 230 and overlaps onto the upper surface 210u of the base 210. The stem 130 preferably includes a ring 131, which is wider than the opening 230. Preferably, the upper surface 210u of the base 210 includes a groove or depression 235 into which the tube gasket 400 partially rests. This allows easier installation of the tube gasket 400 and also increases the likelihood of a proper seal. The ring 131 presses the tube gasket 400 against the base 210. The ring 131 and the base 210 preferably seal to air pressure of at least 30 inches of water gage.

Alternatives to the embodiment of FIG. 5 are within the scope of the invention. For example, although the opening 230, the ring 131 and the tube gasket 400 are shown as substantially circular, other shapes may be used. Furthermore, although the tube gasket 400 is shown disposed between the ring 131 and the base 210, if the ring 131 were smaller than the opening 230, the ring 131 could press the tube gasket 400 against the wall 310, so long as the ring 131 was larger than the insertion hole 330 (see FIG. 1).

Between the various sealing means and the materials of the cover 220 and base 210, the germicidal lamp 1 is NEMA Type 4X compliant. Thus, the germicidal lamp may be installed on exposed, outdoor ductwork and other HVAC components. This is particularly beneficial with respect to rooftop air conditioning equipment. The base and cover gaskets (seals) must be designed to provide a seal and to do so while compensating for existing or imposed dimensionally irregular surfaces and/or burrs. The "O" ring must seal against the treated vessel to eliminate contaminated air from entering the serviceable interior of the base and to eliminate contamination of the power supply from the formation of dew and/or the deposition of corrosive atmospheres. In addition, the "O" and spring-like hold-down clip combine to provide for the dampening of inherent or transient vibrations as well as accidental mishandling of the quartz device, precluding the possibility of contaminating the treated vessel with quartz debris. The arc, fulcrum point and width, length, material and diameter of the spring-like hold-down device must be suitable to engage a maximum portion of the ring and sufficiently to erect an otherwise limp 18–36" long tube into a 89–91 degree sealable position without the aid of additional tools or force. Of course this must all also be possible from the exterior of the treated vessel.

The base could be caulked permanently to a wall and the cover seal could be constructed of an open cell foam of another compound but the preferred method has been described. The tube could be made to screw into the base or be held by other devices that would require tools other than the human hand to achieve erection and a seal but the preferred method of achieving insertion, erection, dampening and properly sealing, currently known, is described without first entering the treated vessel. Other methods might encourage tube breakage or be impossible to do.

The Tube-Holder

The tube 100 has a mass which the fixture 200 and spring must support. The fixture 200 preferably touches only the stem 130 of the tube 100, and therefore the fixture 200 and spring must support additional torsional forces.

FIG. 5 provides a better view of how the stem 130 fits into the opening 230. The stem 130 preferably comprises a stub 132, a ring 131 and a hub 133. The ring 131, stub 132 and hub 133 preferably are specifically and configuratively formed as a unit and are of a rigid, ultraviolet resistant, heat resistant, insulating material such as ceramic. The stub 132, ring 131 and hub 133 are preferably cross-sectionally round. The hub 133 preferably has a diameter a small amount less than the diameter of the through-hole 230. The ring 131 has a diameter larger than that of the through-hole 230. Accordingly, the ring 131 prevents the tube 100 from slipping (descending) through the through-hole 230. The stub 132 preferably has a diameter smaller than that of the ring 131 and may be of the same diameter as the hub 133.

FIG. 5 shows the ring 131 having a first surface 131a, a second surface 131b and a third surface 131c. As mentioned, the stub 132 has a smaller diameter than the ring 131. The first surface 131a comprises the circular flat surface of the ring 131, which is around the stub 132. The second surface 131b comprises the ring's cylindrical surface. The third surface 131b is opposite the first surface 131a. As mentioned, the hub 133 has a smaller diameter than the ring 131. The third surface 131c comprises the circular flat surface of the ring 131, which is around the hub 133.

The stub 132 has a surface 132a comprising the stub's cylindrical surface.

The hub 133 has a surface 133a comprising the hub's cylindrical surface.

The tube gasket 400 preferably has a ring shape. The tube gasket 400 prevents the ring 131 from touching the first wall 210 and acts as a shock absorber and vibration damper. Thus, pressure applied across the tube 100 is absorbed by compression of the tube gasket 400. This prevents damage to the tube 100. The tube gasket 400 also provides a soft, smooth surface against which the envelope 110 presses during and after insertion and removal of the tube 100.

Figure 6:
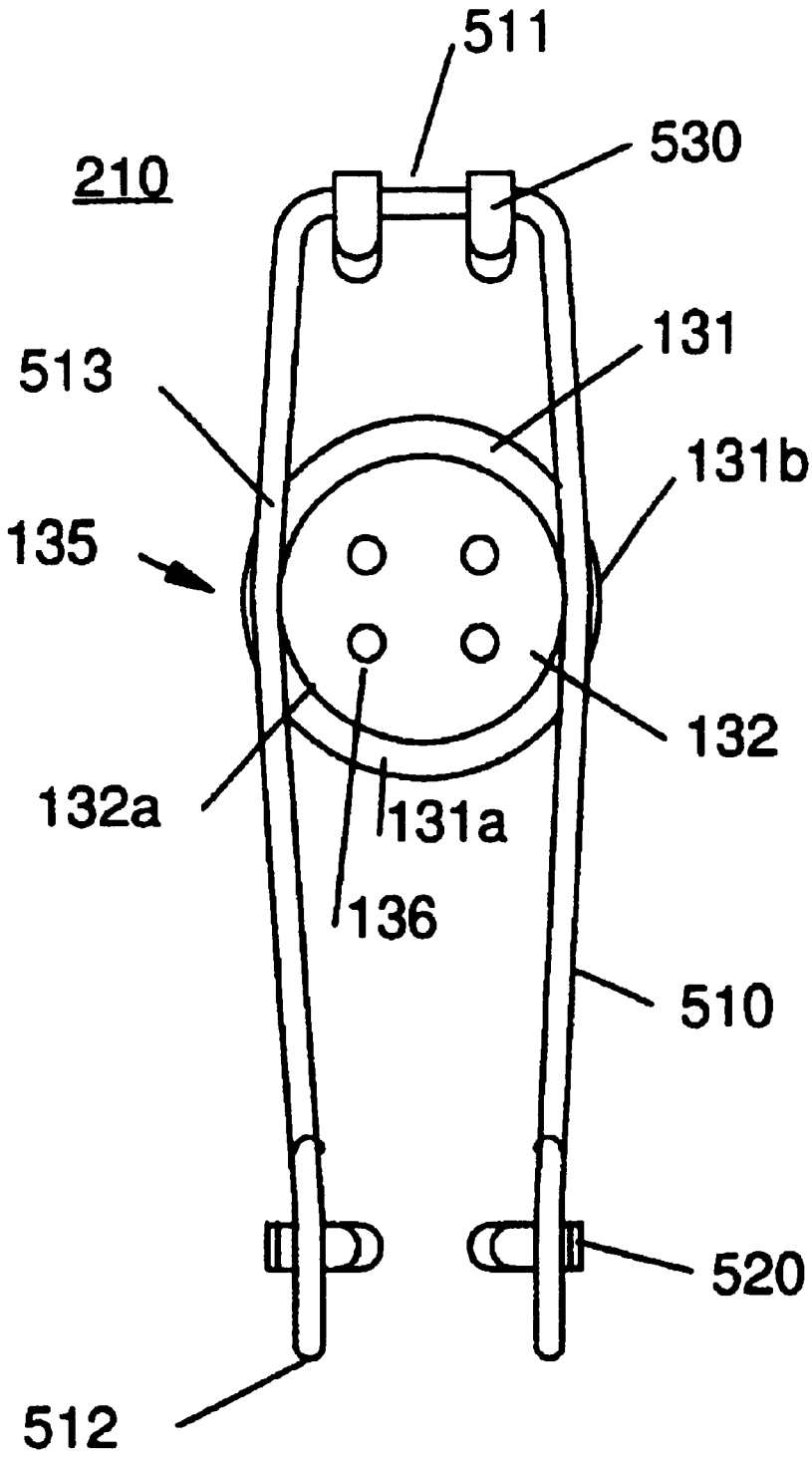
FIG. 6 is a partial outside view of the tube holder in accordance with the invention.

Referring now to FIG. 6, there is shown an embodiment of the tube-holder of the invention. The tube-holder can be seen to be holding the stem 135 in place. The tube-holder is a part of the fixture 200 and is disposed at the opening 230. The tube-holder preferably comprises a spring clamp. The spring clamp comprises a spring 510, two mounts 530 and two stops 520.

The spring 510 preferably comprises wire, such as spring steel bent in a substantially U shape. The stem of the spring's U 511 is fixed by the mounts 530 to the first wall 210 preferably just above the through-hole 230. In FIG. 4, the through-hole 230 is concealed by the stem 135. The spring 510 is preferably flat except for ends 512 which are preferably formed into small circles perpendicular to the U 511. The spring 510 includes a central portion 513 having a surface 513a.

The mounts 530 allow the spring 510 to rotate such that the spring 510 can be pivoted about the mounts 530 from a position substantially parallel to the first wall 210 to a position substantially perpendicular and beyond to the first wall 210.

The stops 520 hold the spring 510 in compression and parallel to the first wall 210. The stops 520 preferably comprise hooks, with one part of the hook fixed to the first wall 210 and the other part of the hook raised above and somewhat parallel to the first wall 210.

To put the spring 510 in the position shown, the ends 512 are pressed toward one another to reduce the distance between them to less than the distance between the stops 520. Preferably, the ends 512 have a cross-sectional area, which allows a person to squeeze them with his or her fingers. In particular, a person places their thumb against one end 512 and their forefinger against the other end 512 and squeezes the thumb and forefinger together. This causes the ends 512 to be moved together (against the spring's naturally tension) so that the ends 512 are close enough to slip into the stops 520. The ends 512 are therefore pressed against the first wall 210 and slid into the hooks of the stops 520. The stops 520 are positioned such that the spring 510 will be in slight compression when inserted into the stops 520.

Both the mounts 530 and the stops 520 may be formed from the first wall 210 itself. That is, they may be formed by cutting tabs into the first wall 210 and lifting the tabs away from the wall a desired distance. The tabs which comprise the mounts 530 are bent around the spring's U 511 to firmly hold the spring's U 511. The tabs which comprise the stops 520 are raised to allow the ends 512 to slip in and out.

When the tube 100 is in place in the fixture 200 as shown in the figures, the central portion 513 of the spring 510 wraps around the surface 132a of the stub 132 and the surface 513a presses against the stub 132. Preferably, the distance between stops the 520 is less than the diameter of the stub 132. More preferably, the distance between the stops 520 is less than the length of the U 511.

The central portion 513 of the spring 510 also lays over the second surface 131b of the ring 131. Because the mounts 530 and stops 520 are mounted on the first wall 210, and the ring 131 has some thickness which puts its surface above the first wall 210, the central portion 513 must also bend around the ring 131. This is better seen from FIG. 6, which shows a partial top cut-away view of the tube holder. As can be seen, the central portion 513 of the spring 510 becomes somewhat concave as its bends over the first surface 131a of the ring 131. FIG. 5 also shows a socket 245 coupled to the stem 135 to provide electrical connection to the electrodes 136 (FIG. 6).

The stub 132 and the ring 131 need not be cylindrical as shown. However, the stub 132 must include a surface (such as surface 132a) against which the central portion 513 of the spring 510 can press. The ring 131 must include a surface (such as surface 131a) against which the central portion 513 of the spring 510 can press. Also, the stem 135 must include a surface (such as surface 132c) which will prevent the tube 100 from passing entirely through the through hole 230. Accordingly, the stub 132 and ring 131 may be cross-sectionally square or some other shape, and the stub 132 may include an indentation into which the central portion 513 may fit.

The tube-holder of the invention provides a number of benefits. First, it permits fast and simple insertion and removal of the tube 100. Pressure from the spring 510 against the ring 131 holds the tube 100 in place laterally. Pressure from the spring 510 against the stub 132 also holds the tube 100 in place longitudinally. As an added benefit, the tension and compression of the spring clamp with the gasket absorbs shocks and vibration which might be applied to the tube 100. In particular, it has been found that the gasket, by damping vibration, significantly extends tube life.

Another and more important unexpected benefit is that the tube 100 may be inserted by a technician without the technician touching the envelope 110. Whenever a human touches the envelope 110, oils from the hands are deposited on the envelope 110 and lead to degradation of the envelope, which alter and obstruct UV output. If the envelope 110 is touched during installation, it must be cleaned before the tube 100 is energized. Since, in many installations, a technician will not be able to access the interior of a duct to clean the envelope 110 except with great difficulty, this is quite important. In many installations, the interior of the duct can only be accessed by improperly opening a wall or cutting open the duct. Since only the stem 135 is touched during installation of the disclosed embodiment, the envelope 110 remains clean.

Other types of tube-holders are also within the scope of the invention. These tube-holders share the desirable features of the disclosed tube holder in that they permit fast and simple insertion and removal of the tube, permit installation and removal of the tube without touching the envelope, and absorb shocks and vibration. Examples of alternative tube holders include tube holders having a twist-lock seating and a bayonet seating. The twist-lock tube holder has the added benefit of one-handed installation.

As an alternative to the tube-holder of FIGS. 5 and 6, the tube-holder may be attached to the cover 220 of the fixture 200. Such a tube-holder would be positioned in the cover 220 such that, when the cover 220 is closed onto the base 210 of the fixture 200, the tube-holder also engages the stem 130 of the tube 100 and holds the tube 100 firmly in place. This alternative tube-holder preferably includes an electrical connector, which engages the electrodes in the stem 130 of the tube 100 when the tube-holder engages the stem 130.

Installation

Installing the tube 100 into the fixture 200 involves the following steps:

1. Open the cover 220 to reveal the interior 260 of the fixture 200.
2. If the spring clamp is closed, open the spring clamp. This is done by squeezing the ends 512 until they clear the stops 520, then pulling the ends 512 away from the first wall 210, 180 degrees.
3. Holding the stem 130, insert the free end 120 of the tube 100 through the opening 230 until the ring 131 presses against the tube gasket 400. Preferably, the tube gasket 400 may be slid onto the hub 133 until it reaches the ring 131 before the free end 120 is inserted through the through-hole 230.
4. Flip both ends' 512, approaching 180 degrees or back down toward the first wall 210 so that the central portion 513 slips around the surface 132a of the stub 132.
5. Press the ends 512 together with the thumb and forefinger so surface 513a of the central portion presses against the surface 132a and the central portion 513 bends around the stub 132.
6. Continue pressing the ends 512 together until the distance between the ends 512 is less than the distance between the stops 520.
7. Press the ends 512 down against the first wall 210 so that the central portion of the spring 510 presses against the first surface 131a and bends around the ring 131 and the ends 512 slip into the stops 520.
8. Release the ends 512 so that they expand back out and press against the stops 520.
9. Push the socket 600 onto the stem 135.
10. Installing the germicidal lamp 1 involves the following steps:
11. Open a hole 330 in the wall 310 having a diameter just slightly larger than the diameter of the hub 133.
12. With the tube 100 already installed in the fixture 200 as described above, insert the free end 100 through the hole 330 until the through-hole 230 self indexes into the created hole 330.
13. Rotate and/or adjust the fixture to the desired rotational location and mount the fixture on the outside of the duct/unit wall using self-tapping screws or other suitable fasteners and electrically connect the fixture to available power.

Once installed, a germicidal lamp provides numerous benefits. The ultraviolet light kills, degrades and vaporizes microorganisms and other organic material, which naturally forms over time on a heat exchanger. As this material is eliminated, pressure drop across the heat exchanger is decreased, airflow usually increases and the heat exchange efficiency (net capacity) is increased. In particular, there is no organic matter to impair heat transfer and airflow from and through a coil, and therefore less energy is used by an HVAC system to circulate air and exchange heat a given amount of heat from it as the typical restrictions are reduced. Furthermore, the ultraviolet radiation controls health hazards which originate from or pass through a cooling or heating system including contributions made by a systems drain pan.

The invention has numerous benefits and advantages over the prior art. One benefit is that the invention can amount to significant energy savings in a cooling or heating system. UVC does not require an increase in run time, the lowering of cooling coil temperature or raising the heating temperature to attain a given temperature under a given set of operating conditions, thereby avoiding the additional consumption of a significant amount of energy. UVC does not require modifications to fan speed or motor horsepower, thereby further avoiding consumption of a significant amount of energy. Using standard life cycle analysis, UVC energy proves to be the least expensive method of cleaning an installed heat exchanger. UVC energy can also maximize the useful life of a heat exchanger. UVC can return more coil surface and open area, and can thus increase heat transfer and airflow more than any other method. Health hazards, odors and airborne microorganisms are also controlled.

Properly designed HVAC-type germicidal devices, such as our VC Emitters, can be installed without interruption of the normal operation of an HVAC system. Because of the proven energy-saving abilities of application method, other more expensive and less beneficial energy-saving devices may not be needed. The germicidal lamp of the invention can be installed outdoors without opening or compromising equipment.

Once the germicidal lamps are installed in the manner disclosed in our other patent applications:

Heat exchanger pressure drop goes back to "as new."

Heat exchanger airflow goes back to "as built" or "as installed."

Heat exchanger cleanliness goes back to "as built" or "as installed."

Heat exchanger capacity goes back to "as built" or "as installed."

Heat exchanger cleaning is no longer required.

Space humidity and temperature are more easily controlled.

Heat exchangers no longer seed the ductwork or space with viable microbes or other bioaerosols.

Drain pans no longer require biocidal treatment.

Drain pans no longer entrain microorganisms and water into the air stream.

Coil and drain pan contaminants are ionized and degraded (vaporized).

The drain pan will drain freely, eliminating standing water and potential overflow damage.

The germicidal lamps clean the coil and drain pan to "as new" specifications, completely returning heat exchange efficiency (heat removal) and pressure drop (airflow) to original values.

The germicidal lamps keep the heat exchanger in this condition for the life of the system.

The process is not destructive to the heat exchanger's surface or any other inorganic material.

The process requires no hazardous chemicals.

The process is environmentally friendly, as it adds nothing to the air or drainage system.

The germicidal lamps do the job continuously without shutting down the system or vacating the building.

A complete installation of germicidal lamps can cost less than any other method purported to achieve the same results.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

It is claimed:

1. A germicidal lamp for harsh environments adapted to be mounted on a wall, the wall having an insertion opening, the germicidal lamp comprising:

a low pressure germicidal tube which when energized emits UVC without substantial ozone and can withstand skin-effect cooling, the tube including an envelope and a stem, and a fixture comprising a cover, a base and a tube holder, wherein the base has an upper surface and a lower surface, the lower surface of the base seals against the wall to thereby prevent splashing water, hose-directed water, ice formations, wind, dirt, rain and environmental corrosion to pass there through, the cover is at least partially detachable from the base so that the cover can be moved from a first position wherein the cover covers the upper surface to a second position wherein the cover is at least partially separated from the base to at least partially expose the upper surface of the base, the cover and the upper surface of the base define an interior space within the fixture, the cover seals tightly to the base to thereby prevent splashing water, hose-directed water, ice formations, wind, rain and environmental corrosion from entering the interior space of the fixture, the base includes an opening through which the envelope of the tube is passed for installation of the tube in the fixture and removal of the tube from the fixture, installation of the tube causes a flange on the tube stem to sealingly engage the base which seals the opening in the base of the fixture from air flow into the fixture, the tube-holder, including an engaging surface adapted to engage and secure the stem of the tube, after the envelope has been inserted through the opening in the base of the fixture, the cover and the base include exterior surfaces which are resistant to splashing water, hose-directed water, ice formations, wind, rain and environmental corrosion.

2. The germicidal lamp for harsh environments adapted to be mounted on a wall of claim 1 wherein the tube comprises an elongate hollow cylinder.

3. The germicidal lamp for harsh environments adapted to be mounted on a wall of claim 1 wherein the tube is adapted such that UVC output from the tube peaks when an air flow of between 200 cfm and 600 cfm at between 30° F. and 65° F. is passed across the tube.

4. The germicidal lamp for harsh environments adapted to be mounted on a wall of claim 3 wherein the tube is adapted such that UVC output from the tube peaks when an air flow of 400 cfm at 55° F. is passed across the tube.

5. The germicidal lamp for harsh environments adapted to be mounted on a wall of claim 1 wherein the tube emits UVC of at least 10-$\mu W/cm^2$ per inch arc length at one meter when an airflow of between 100 and 800 cfm is passed across the tube.

6. The germicidal lamp for harsh environments adapted to be mounted on a wall of claim 1 wherein the tube emits UVC of at least 10 $\mu W/cm^2$ per inch arc length at one meter when an air flow of between 0° F. and 70° F. is passed across the tube.

7. The germicidal lamp for harsh environments adapted to be mounted on a wall of claim 1 having a weight of less than two lbs.

8. The germicidal lamp for harsh environments adapted to be mounted on a wall of claim 1 wherein the cover and the base of the fixture are separable.

9. The germicidal lamp for harsh environments adapted to be mounted on a wall of claim 1 wherein the cover and the base of the fixture have a clamshell design.

10. The germicidal lamp for harsh environments adapted to be mounted on a wall of claim 1 wherein the base of the fixture includes the tube-holder.

11. The germicidal lamp for harsh environments adapted to be mounted on a wall of claim 10 wherein the tube-holder comprises a spring clamp attached to the upper surface of the base of the fixture around the opening in the base, the spring clamp comprising a spring, a mount and two stops, the spring comprising wire in a substantially flat U shape, the stem of the spring's U being fixed by the mount to the upper surface of the base adjacent the opening such that the arms of the U are disposed on opposite sides of the opening, the mount allowing the spring to rotate such that the spring can be pivoted about the mount between a position substantially parallel to the upper surface to a position substantially perpendicular to the upper surface, the stops holding the spring in compression and parallel to the upper surface, wherein the spring clamp wraps at least partially around the stem of the tube and presses the stem against the upper surface of the base of the fixture and thereby holds the tube in place and the tube in the fixture.

12. The germicidal lamp for harsh environments adapted to be mounted on a wall of claim 1 wherein the tube-holder is attached to the cover of the fixture, wherein the tube-holder is positioned in the cover such that, when the cover is closed onto the base of the fixture, the tube-holder also engages the stem of the tube and holds the tube firmly in place.

13. The germicidal lamp for harsh environments adapted to be mounted on a wall of claim 1 wherein the tube-holder includes an electrical connector which engages at least one electrode in the stem of the tube when the tube-holder engages the stem.

14. The germicidal lamp for harsh environments adapted to be mounted on a wall of claim 1, wherein installation of the tube causes the a flange on tube stem to sealingly engage the base, forming a seal, the seal is adapted to be seated around the opening in the base to thereby prevent splashing water, hose-directed water, ice formations, wind, dirt, rain and environmental corrosion to pass there through.

15. The germicidal lamp for harsh environments adapted to be mounted to a wall of claim 1 wherein the lower surface of the base seals against a wall, creating a seal between the fixture and the wall that can withstand air pressure of at least 15 inches of water gage.

16. The germicidal lamp for harsh environments adapted to be mounted on a wall of claim 1, the cover and the base of the fixture defining an interior space, the fixture further comprising a power supply adapted to convert an input power source into a form appropriate for the tube.

17. The germicidal lamp for harsh environments adapted to be mounted on a wall of claim 1 further including an electrical connector disposed within the fixture adapted to electrically engage the stem of the tube, the germicidal lamp further including plural electrical leads attached to the electrical connector and extending outside of the fixture, the leads including piggyback connectors adapted to be connected to an air conditioner's power or fan controller, whereby other connectors on the controller can be removed from the controller and attached to the piggyback connector, and the piggyback can then be attached to the controller in place of the other connector.

18. The germicidal lamp for harsh environments adapted to be mounted to a wall of claim 1, wherein installation of the tube causes a flange of the stem to sealingly engage the base and form a seal between the tube and the fixture that can withstand air pressure of at least 30 inches of water gage.

19. The germicidal lamp for harsh environments adapted to be mounted to a wall of claim 1, wherein the cover seals tightly to the base to form a seal between the cover and the base that can withstand air pressure of at least 20 inches of water gage.

20. An air handling system comprising the germicidal lamp of claim 1.

21. An HVAC system comprising the germicidal lamp of claim 1.

22. A germicidal lamp for harsh environments comprising:

a single-walled tube having a stemmed end with a flange, and a free end and comprising an envelope disposed between the ends having a first cross-sectional shape, a rigid stem secured to the envelope at the stemmed end, the stem including at least one electrode; and a fixture comprising:

a base having an upper surface and a lower surface, the base including an opening through which the envelope of the tube is passed for installation of the tube in the fixture and removal of the tube from the fixture, but through which the stem will not fully pass, the flange on the stemmed end of the tube sealingly engaging the base when the tube is installed, the lower surface of the base sealing against a wall to thereby prevent splashing water, hose-directed water, ice formations, wind, rain and environmental corrosion to pass there through, the base including an exterior surface which is resistant to splashing water, hose-directed water, ice formations, wind, rain and environmental corrosion;

a socket disposed inside of the fixture and electrically coupled to at least one electrode;

a cover which is at least partially detachable from the base so that the cover can be moved from a first position wherein the cover covers the upper surface and the cover can be partially moved away from the base to at least partially expose the upper surface of the base, the cover sealing tightly to the base to thereby prevent splashing water, hose-directed water, ice formations, wind, rain and environmental corrosion from entering the interior space of the fixture, the cover including an exterior surfaces which are resistant to splashing water, hose-directed water, ice formations, wind, rain and environmental corrosion;

a tube holder including an engaging surface adapted to engage and secure the stem of the tube.

23. The germicidal lamp for harsh environments of claim 22, the tube-holder comprising a spring clamp coupled to the primary wall around the opening, the spring clamp comprising a spring, a mount and two stops, the spring comprising wire in a substantially flat U shape, the stem of the spring's U being fixed by the mount to the first wall adjacent the through-hole such that the arms of the U are disposed on opposite sides of the through-hole, the mount allowing the spring to rotate such that the spring can be pivoted about the mount from a position substantially parallel to the first wall to a position substantially perpendicular to the first wall, the stops holding the spring in compression and parallel to the first wall;

wherein the spring clamp wraps at least partially around the stem and presses the stem into the primary wall and thereby holds the tube in place.

24. The germicidal lamp for harsh environments of claim 22 wherein the tube comprises a low pressure germicidal tube which, when energized, emits UVC without substantial ozone and can withstand skin effect cooling in an air flow of between 200 cfm and 600 cfm at between 30° F. and 65° F.

25. The germicidal lamp for harsh environments adapted to be mounted on a wall of claim 22 wherein the tube emits UVC of at least 10-$\mu W/cm^2$ per inch arc length at one meter when an airflow of between 100 and 800 cfm is passed across the tube.

26. The germicidal lamp for harsh environments adapted to be mounted on a wall of claim 22 wherein the tube emits UVC of at least 10 $\mu W/cm^2$ per inch arc length at one meter when an air flow of between 0° F. and 70° F. is passed across the tube.

27. The germicidal lamp for harsh environments adapted to be mounted on a wall of claim 22 having a weight of less than two pounds.

28. The germicidal lamp for harsh environments adapted to be mounted to a wall of claim 22 wherein the lower surface of the base sealing against a wall forms a seal between the fixture and the wall that can withstand air of at least 15 inches of water gage.

29. The germicidal lamp for harsh environments adapted to be mounted to a wall of claim 22, wherein the flange on the stemmed end of the tube sealing engaging the base when the tube is installed forms a seal between the tube and the fixture that can withstand air pressure of at least 30 inches of water gage.

30. The germicidal lamp for harsh environments adapted to be mounted to a wall of claim 22, wherein the cover sealingly tight to the base forms a seal between the cover and the base that can withstand air pressure of at least 20 inches of water gage.

31. An air handling system comprising the germicidal lamp of claim 22.

32. An HVAC system comprising the germicidal lamp of claim 22.

*33. A germicidal lamp for harsh environments comprising:*

*means for emitting UVC without substantial ozone and for withstanding skin-effect cooling, the emitting means including an envelope and a stem*

*a fixture comprising*

*means for sealing against a wall to thereby prevent splashing water, hose-directed water, ice formations, wind, dirt, rain and environmental corrosion to pass there through*

*means for opening the fixture*

*means for sealing the fixture tightly to thereby prevent splashing water, hose-directed water, ice formations, wind, rain and environmental corrosion from entering the interior space of the fixture*

*means for allowing the emitting means to be passed through the fixture for installation and removal*

*means for sealing the fixture from air flowing into the fixture*

*means for engaging and securing the emitting means*

*wherein the emitting means includes means for causing UVC output to peak when an airflow of 400 cfm at 55° F. is passed across the emitting means.*

*34. A germicidal lanp for harsh environments comprising:*

*means for emitting UVC without substantial ozone and for withstanding skin-effect cooling, the emitting means including an envelope and a stem*

*a fixture comprising*

*means for sealing against a wall to thereby prevent splashing water, hose-directed water, ice formations, wind, dirt, rain and environmental corrosion to pass there through*

*means for opening the fixture*

*means for sealing the fixture tightly to thereby prevent splashing water, hose-directed water, ice formations, wind, rain and environmental corrosion from entering the interior space of the fixture*

*means for allowing the emitting means to be passed through the fixture for installation and removal*

*means for sealing the fixture from air flowing into the fixture*

*means for engaging and securing the emitting means*

*wherein the emitting means includes means for causing UVC output to peak when an air flow of between 200 cfm and 600 cfm at between 30° F. and 55° F. is passed across the emitting means*

*means for sealing the fixture against the wall, creating a seal between the fixture and the wall that can withstand air pressure of at least 15 inches of water gage.*

*35. A germicidal lamp for harsh environments comprising:*

*means for emitting UVC without substantial ozone and for withstanding skin-effect cooling, the emitting means including an envelope and a stem*

*a fixture comprising*

*means for sealing against a wall to thereby prevent splashing water, hose-directed water, ice formations, wind, dirt, rain and environmental corrosion to pass there through*

*means for opening the fixture*

*means for sealing the fixture tightly to thereby prevent splashing water, hose-directed water, ice formations, wind, rain and environmental corrosion from entering the interior space of the fixture*

*means for allowing the emitting means to be passed through the fixture for installation and removal*

*means for sealing the fixture from air flowing into the fixture*

*means for engaging and securing the emitting means*

*wherein the emitting means includes means for causing UVC output to peak when an air flow of between 200 cfm and 600 cfm at between 30° F. and 55° F. is passed across the emitting means*

*means for sealing the fixture to withstand air pressure of at least 30 inches of water gage.*

* * * * *